(12) United States Patent
Yoo et al.

(10) Patent No.: US 7,599,048 B2
(45) Date of Patent: Oct. 6, 2009

(54) OPTICAL EMISSION SPECTROSCOPY PROCESS MONITORING AND MATERIAL CHARACTERIZATION

(75) Inventors: Woo Sik Yoo, Palo Alto, CA (US); Kitaek Kang, Dublin, CA (US)

(73) Assignee: WaferMasters, Inc., San Jose, CA (US)

( * ) Notice: Subject to any disclaimer, the term of this patent is extended or adjusted under 35 U.S.C. 154(b) by 250 days.

(21) Appl. No.: 11/689,419

(22) Filed: Mar. 21, 2007

(65) Prior Publication Data
US 2008/0192250 A1 Aug. 14, 2008

Related U.S. Application Data

(63) Continuation-in-part of application No. 11/673,306, filed on Feb. 9, 2007.

(51) Int. Cl.
*G01J 3/443* (2006.01)
*G01N 21/63* (2006.01)

(52) U.S. Cl. .................................. 356/72; 356/318

(58) Field of Classification Search ............. 356/72, 356/318; 438/16
See application file for complete search history.

(56) References Cited

U.S. PATENT DOCUMENTS

| 6,532,068 | B2 * | 3/2003 | Detalle et al. ............... 356/318 |
| 6,873,419 | B2 * | 3/2005 | Detalle et al. ............... 356/479 |
| 7,440,097 | B2 * | 10/2008 | Benicewicz et al. ......... 356/316 |

* cited by examiner

*Primary Examiner*—F. L Evans
(74) *Attorney, Agent, or Firm*—Haynes & Boone, LLP.

(57) ABSTRACT

Methods and systems for control and monitoring processing of semiconductor materials with a focused laser beam. Laser light may be focused on a sample to excite optical emission at the sample surface during processing, which may include laser processing. Optical emission spectra produced may be analyzed for various properties effectively during the process. For example, process effects such as chemical composition analysis, species concentration, depth profiling, homogeneity characterization and mapping, purity, and reactivity may be monitored by optical spectral analysis. The wavelength may be selected to be appropriate for the process effect chosen.

32 Claims, 9 Drawing Sheets

US 7,599,048 B2

OPTICAL EMISSION SPECTROSCOPY PROCESS MONITORING AND MATERIAL CHARACTERIZATION

CROSS REFERENCE TO RELATED APPLICATIONS

This application is a continuation-in-part application of U.S. patent application Ser. No. 11/673,306, entitled "FOCUSED LASER BEAM PROCESSING", filed on Feb. 9, 2007.

BACKGROUND

1. Field of Invention

This disclosure generally relates to process characterization, monitoring and control of semiconductor substrates with a focused laser beam in conjunction with laser and other processing methods.

2. Related Art

A number of techniques are available for chemical analysis of in situ semiconductor processes that incorporate some form of spectroscopy to assess species concentrations affecting the process. While each may have particular advantages, there are also disadvantages whereby incorporation of the method in situ is difficult or not possible. In many cases, evacuated chamber low pressure operation is required. In addition, many such processes are destructive of at least portions of the substrate, and therefore may not enable comprehensive mapping of process characterization. For example, inductively coupled plasma mass spectroscopy (ICP-MS) requires low pressure plasma discharge to enable mass spectroscopy. Glow discharge mass spectroscopy (GDMS) also requires low pressure. In addition, the sample must either be conductive or requires a conductive coating, which complicates process analysis and fabrication. Sputtering Optical emission spectroscopy (SOES) requires low pressure operation to sputter material for depth profiling. Auger electron spectroscopy (AES), secondary ion mass spectroscopy (SIMS), and X-ray photoelectron spectroscopy (XPS) also all require low pressure for material sputtering and mass spectroscopy. The analytical sensor systems mentioned above all require complex low pressure environments and involve some form of mass transfer (i.e., sputtering, mass spectroscopy) or X-ray production equipment. All-optical techniques may be easier to implement, requiring access to the process environment only through transparent windows or via optical fiber, and therefore are not required to be vacuum-compatible. Additionally, an optical method of spectroscopy that does not also require some form of excitation beyond that which results in the normal course of processing would be advantageous.

Focused laser beams have found applications in drilling, scribing, and cutting of semiconductor wafers, such as silicon. Marking and scribing of non-semiconductor materials, such as printed circuit boards and product labels are additional common applications of focused laser beams. Microelectromechanical systems (MEMS) devices are laser machined to provide channels, pockets, and through features (holes) with laser spot sizes down to 5 μm and positioning resolution of 1 μm. Channels and pockets allow the device to flex. All such processes rely on a significant rise in the temperature of the material in a region highly localized at the laser beam point of focus.

The foregoing applications, however, are all, to some degree, destructive, and relate generally to focused laser beams at power densities intended to ablate material. Thus, there is a need to provide and control laser beams to achieve process monitoring for electronic and/or optical device fabrication on semiconductor wafers that are non-destructive, and which do not interfere with, or are compatible with other laser-based and/or non-laser manufacturing processes.

SUMMARY

Methods and systems of characterization and/or monitoring semiconductor material and device processing with focused laser beams are disclosed. Specifically, in accordance with an embodiment of the disclosure, a method of monitoring the processing of semiconductor substrates, materials and devices includes providing a laser beam of a selected wavelength and a selected peak power. The laser beam may be continuous (CW) to a selected average power or may be modulated to provide pulses of a discrete time pulse width. The laser beam is focused at the surface plane of the semiconductor material. The total energy in each laser pulse is controlled to a selected value. The laser beam is scanned over the surface of the semiconductor material in a programmed pattern. The laser beam may be focused at a specific depth beneath the surface of the substrate to preferably monitor process effects at said depth. Process monitoring is accomplished by illuminating the substrate and collecting scattered optical emission that includes spectroscopic information descriptive of the composition of the substrate material. The method may be used to monitor and control the process. The method may further be integrated with laser-based processing methods.

BRIEF DESCRIPTION OF THE DRAWINGS

Like reference symbols in the various drawings indicate like elements.

DETAILED DESCRIPTION

Figure 1:
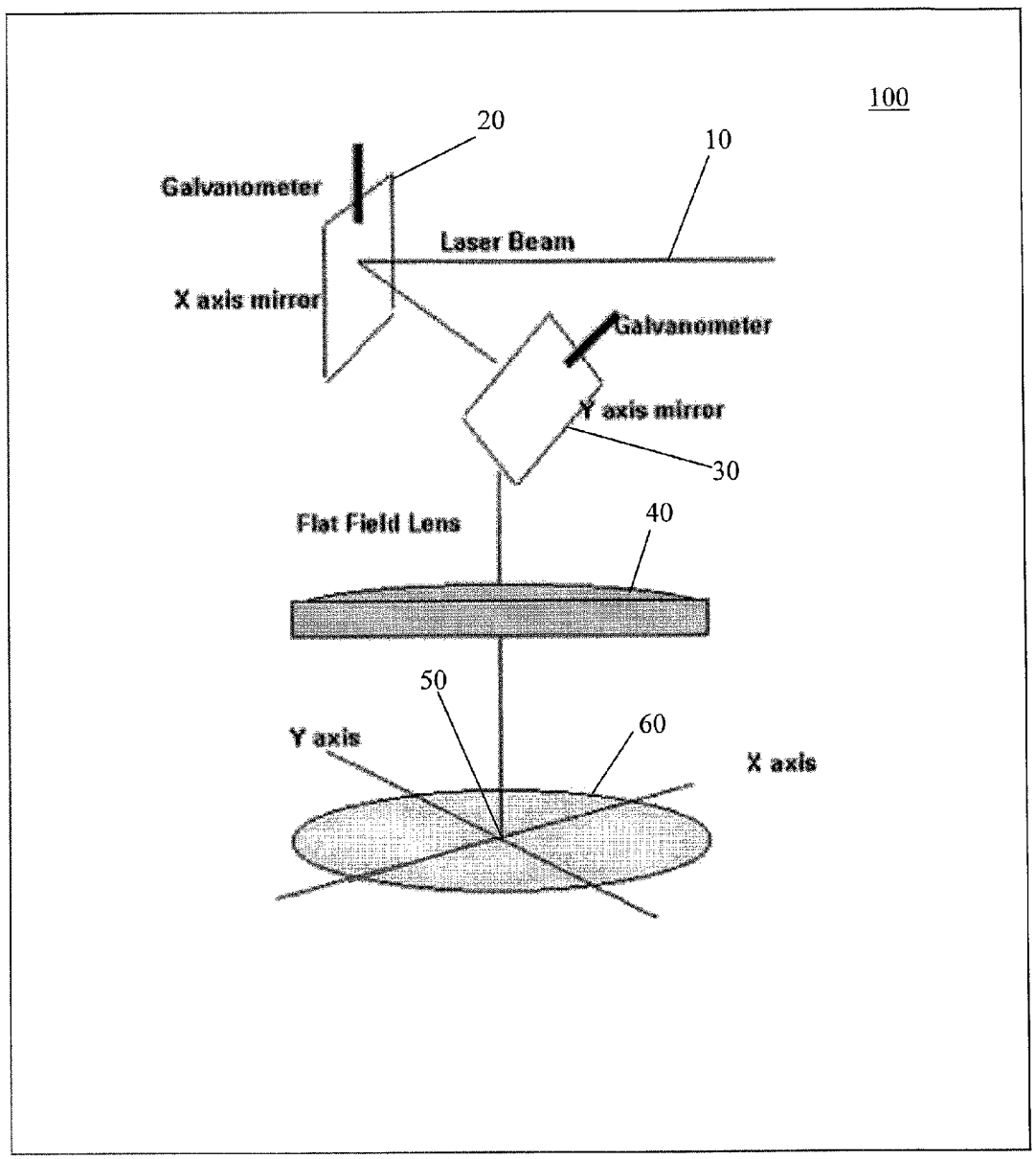
FIG. 1 is a drawing of a galvanometric beam scanner, in accordance with an embodiment of the disclosure.

FIG. 1 is a drawing of a galvanometric beam substrate scanning system 100 for directing a focused laser beam at a semiconductor substrate during a processing step of device manufacturing. A collimated laser beam 10 is directed to a first mirror galvanometer 20 configured to scan laser beam 10, for example, in an axial direction about a first axis. Laser beam 10 is then directed toward a second mirror galvanometer 30 configured to scan laser beam 10, for example, in an axial direction about a second axis, which is perpendicular to the first axis. The effect of the two galvanometer mirrors 20 and 30 is to scan laser beam 10 in perpendicular X and Y directions in the plane of a semiconductor substrate 60. Laser beam 10 is directed by the combination of mirror galvanometers 20 and 30 through a flat field focusing lens 40. The function of flat field lens 40 is to bring laser beam 10 to a focused spot 50 at the surface of semiconductor substrate 60 with minimum distortion of the focused beam across the entire area to be scanned. Lens 40 may be a single lens or, alternatively a compound system of lenses configured to accomplish the same objective. Programmable controls (not shown) of mirror galvanometers 20 and 30 then position focused spot 50 at specified locations on substrate 60.

Figure 2:
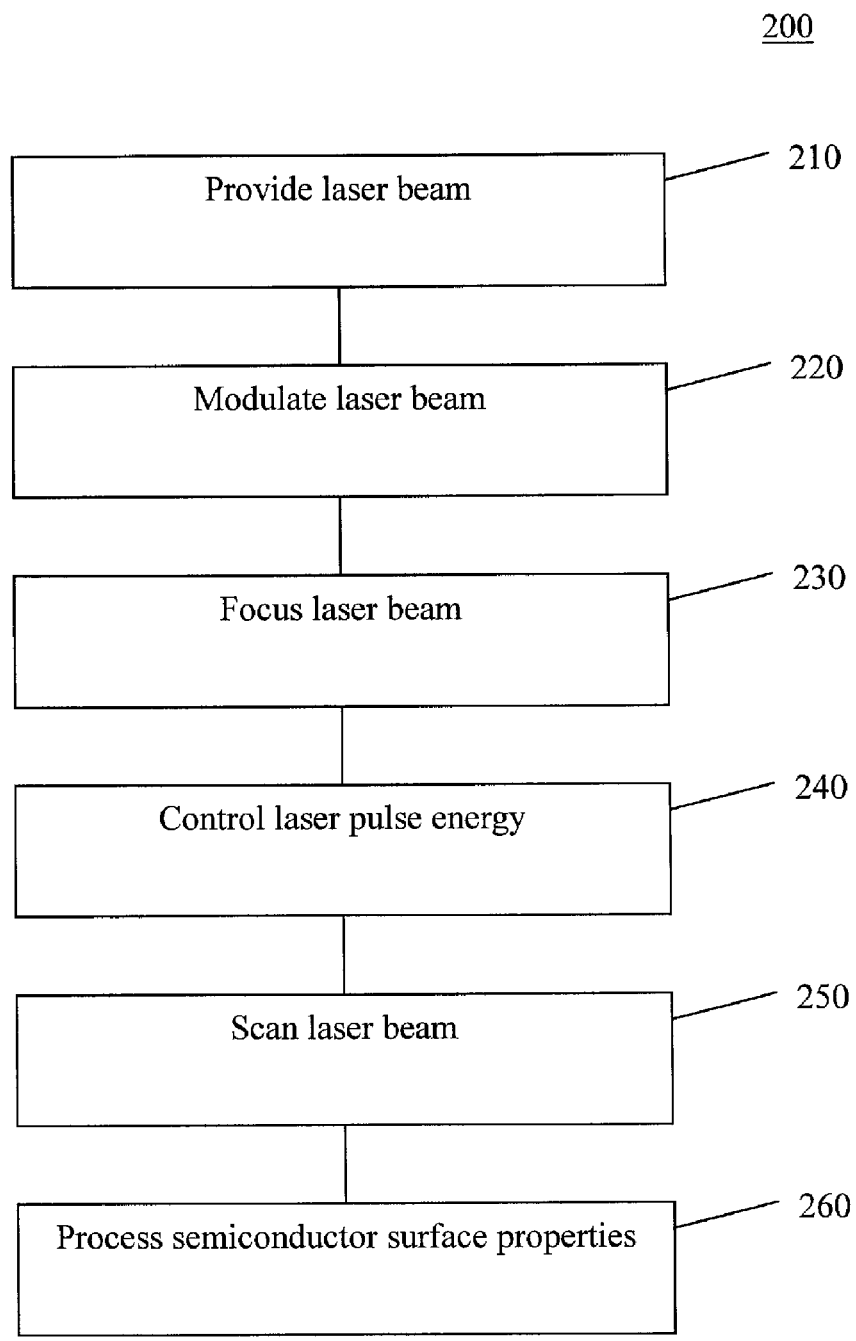
FIG. 2 is a diagram of the method of processing semiconductor materials and devices in accordance with an embodiment of the disclosure.

FIG. 2 is a diagram of the method of laser processing 200 semiconductor materials and devices in accordance with an embodiment of the disclosure. Laser beam 10, as provided in block 210, may be selected to have a wavelength appropriate to the process application. For many such possible applications, the wavelength may range, for example, from 140 nanometers to 3 microns; however, wavelengths beyond this range may be useful for some processes. Laser beam 10 may be continuous or, alternatively, it may be pulsed. Regardless, laser beam 10 may require a selected peak power to meet the requirements of a particular process application.

For the required application, laser beam 10 may be appropriately modulated (block 220). Modulation may include providing pulses of laser light where the pulse width may range from approximately 10 femtoseconds to approximately 100 milliseconds, depending on the process application. A pulse repetition rate may be selected to provide laser energy to the surface of the semiconductor substrate at a selected average power and peak pulse power. The selected average power is generally the product of the pulse width times the peak power times the fraction corresponding to a selected duty cycle, assuming the peak power is constant over the length of the pulse. The duty cycle is the percentage corresponding to the fraction of the pulse width divided by the period corresponding to the pulse repetition rate, where the period is the inverse of the pulse repetition rate.

Laser beam 10 may then be focused (block 230) to a preferred beam diameter at a focal plane containing semiconductor substrate 60 with flat field lens 40. Depending on the application, the preferred beam diameter may range from approximately 0.1 micron to 1 millimeter. The "spot" size is dependent on the wave length, the lens aperture, and the optical configuration of the lens relative to the substrate. Lens 40, or in the case of a compound lens optical system, is shown disposed between the system of mirror galvanometers 20 and 30, but may also be disposed elsewhere in the optical beam system.

The beam diameter may be defined in a variety of ways, all of which may substantially serve as definitions of beam diameter. For a circular beam having a Gaussian profile of intensity, one typical definition specifies the beam diameter according to the radial distance from the beam center at which the power density drops to $1/e^2$ of the power density at the beam center, where e is the natural logarithm base. Another definition, for example, where the intensity of a circular beam is substantially constant over the aperture of the spot size, is the radial distance at which the power density drops to a given percentage of the central power density, such as 50% or 10%. Other definitions of beam diameter may also be acceptable, in accordance with the embodiment of the disclosure. The ultimate requirement is to provide sufficient thermal heating in a highly localized region of the semiconductor substrate or sample, at the surface and to a controlled but sufficient depth, to produce the desired process effect.

The total energy in a single laser pulse is generally the product of the peak power and the pulse width, assuming the power is constant over the pulse width. The total energy in a single laser pulse may be controlled (block 240) by selecting a combination of peak power and pulse width. A typical range of total pulse energy may extend from approximately 1 micro-Joule to 1 Joule, but various process applications may require higher or lower total impulse energy. It is worth noting, as a matter of practicality, when peak laser energy is too low, the thermal conductivity of the semiconductor substrate and any fixture supporting it may result in a negligible rise in temperature. Therefore, peak laser power must be able to overcome thermal conductivity effects to the extent sufficient for the process application. A discussion of the effect of laser pulse width is included below.

Laser beam 10, is directed to scan (block 250) substrate 60 by actuation of mirror galvanometers 20 and 30. The area scanned may range from 7840 nanometer$^2$—on the order of a single focused laser spot 50—to about 400 cm$^2$, potentially the entire area of substrate 60. Scanning may occur over one section of substrate 60 at a time, and may be repeated as necessary, or it may occur over the entire substrate in a single programmed scanning path. It may be advantageous to scan a limited segment area of substrate 60 and then reposition substrate 60, with the aid of a substrate processing station (described below) adapted to translate the location of substrate 60 for a successive scan of another area. In this way, distortions of the optical beam, and consequent degradation of focused spot 50 resulting from large angular excursion that may be required of mirror galvanometers 20 and 30 may be avoided by restricting the scanned field of view required, thereby improving accuracy and uniformity of process performance. Between scanning segments, laser beam 10 may be blocked or otherwise terminated so as not to cause any process effects to occur on substrate 60 in undesirable locations. Alternatively, an entire substrate may be scanned by simultaneous combination of beam scanning and substrate translation.

A large variety of process effects may be accomplished (block 260) using laser beam 10 as focused spot 50. These may include annealing, implant activation, dopant diffusion control, deposition, thin film formation, chemical reaction, curing, baking, and other forms of material modification. The spatial extent to which these effects are achieved may be critically controlled by the size of focused spot 50.

Figure 3:
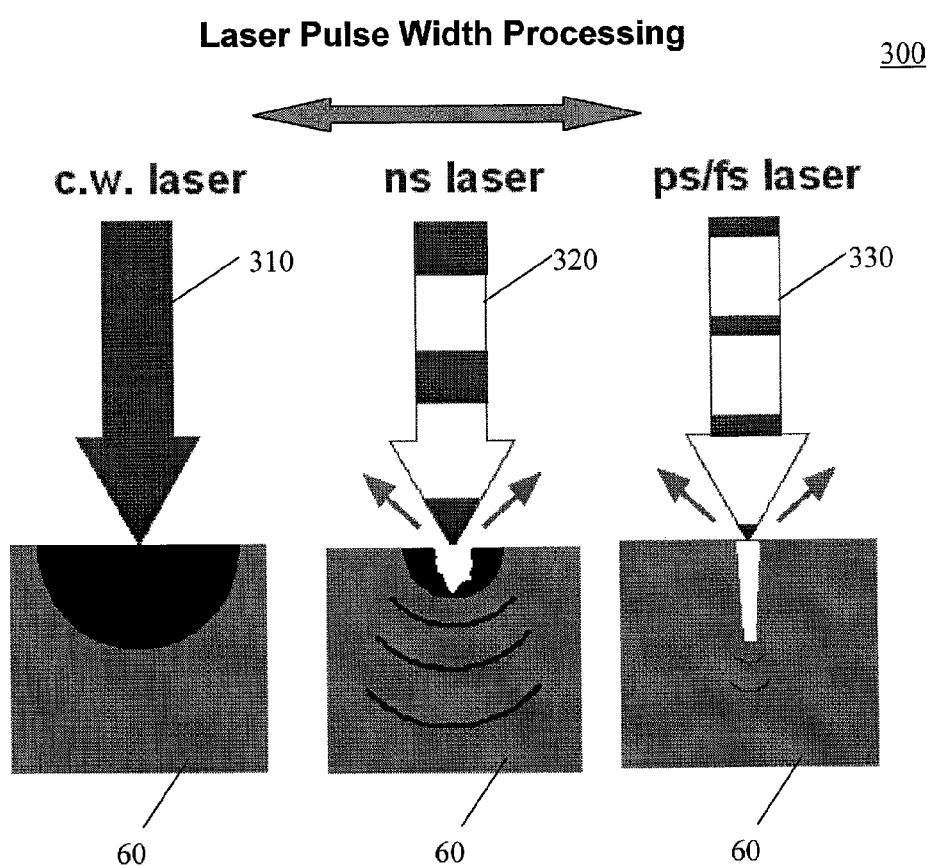
FIG. 3 is an illustration of the effects of laser pulse width in accordance with an embodiment of the disclosure.

As an example of the effect of focused laser scanning, FIG. 3 is an illustration of the effects of laser pulse width processing 300 on substrate 60, and any devices being fabricated therein, in accordance with an embodiment of the disclosure. Substrate 60 may be subjected to laser pulses of various pulse widths. As an example, we consider that each pulse has the same total energy in a given repetition period and the same spot size 50, so that longer pulses have low peak power and density and, conversely, shorter pulses have higher peak power and density. Considering that the pulse width can potentially vary by as much as 11 orders of magnitude, a considerable range of processing possibilities may exist.

At one extreme, the laser may be operating in continuous wave (c.w.) mode 310. Therefore, the peak and average power may be quite low. In this case, a thermal impulse may result in a certain degree of thermal heating that may range from having a negligible effect to being sufficient to cause a process such as annealing or local melting. In the case of a laser pulse of nanosecond (ns) duration 320, the peak power may be correspondingly higher, under the exemplary conditions being assumed. The thermal impulse produced may result in ablative removal, for example, of photo-resist or other deposited material, such as a metallic trace. In addition, the pulse width may be such that thermo-elastic effects result in producing a shock wave that couples to elastic wave generation into substrate 60 as a further means of dissipating the energy deposited by beam 10. In the case of picosecond (ps) or femtosecond (fs) pulses 330, the peak power may be so high and the pulse width so narrow that energy is dissipated in processes such as via drilling of narrow holes with production of ablative material, for example, to enable contact between subsurface layers of substrate 60 and top surface layers currently existing or layers deposited on substrate 60 in subsequent steps. In this case the pulse width may be too short to effectively couple significant energy into elastic waves, and the efficiency of the process effect may thereby be improved.

Figure 4:
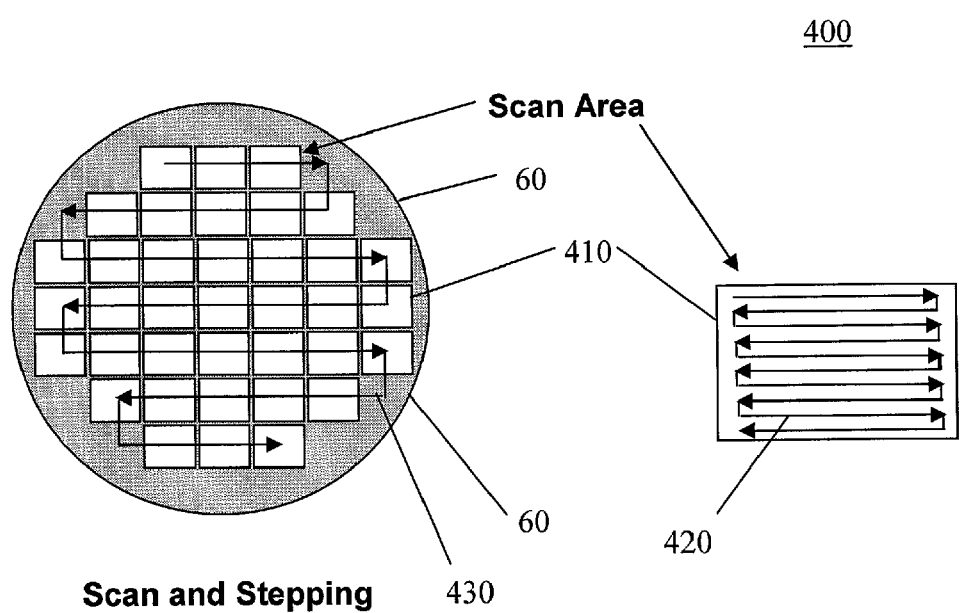
FIG. 4 is an illustration of scanning and stepping in accordance with an embodiment of the disclosure.

FIG. 4 is a drawing illustrating scanning and stepping 400 in accordance with an embodiment of the disclosure. Substrate 60 may contain a plurality of segments 410. Within a single segment 410, substrate scanning system 100 may generate a scanning path 420, such as a raster scan, for focused spot 50 to follow, as well as control various other parameters introduced above, such as the size of focused spot 50, pulse width, duty cycle, peak power, and total pulse energy under the direction of a processor and controller (both not shown, discussed below). Upon completion of scanning path 420 in a first one of segment 410, substrate 60 may be repositioned, i.e., stepped, to locate a second one of segment 410 in the optimal center of the field of view of scanning system 100 and the process repeated, until all selected segments 410 have been scanned and the process effect achieved in each selected segment 410. A stepping path 430 may be provided by the substrate processing station to position substrate 60 accordingly. Stepping path 430 may be an approximate raster scan, as shown, or other suitable stepping or scanning pattern.

Figure 5:
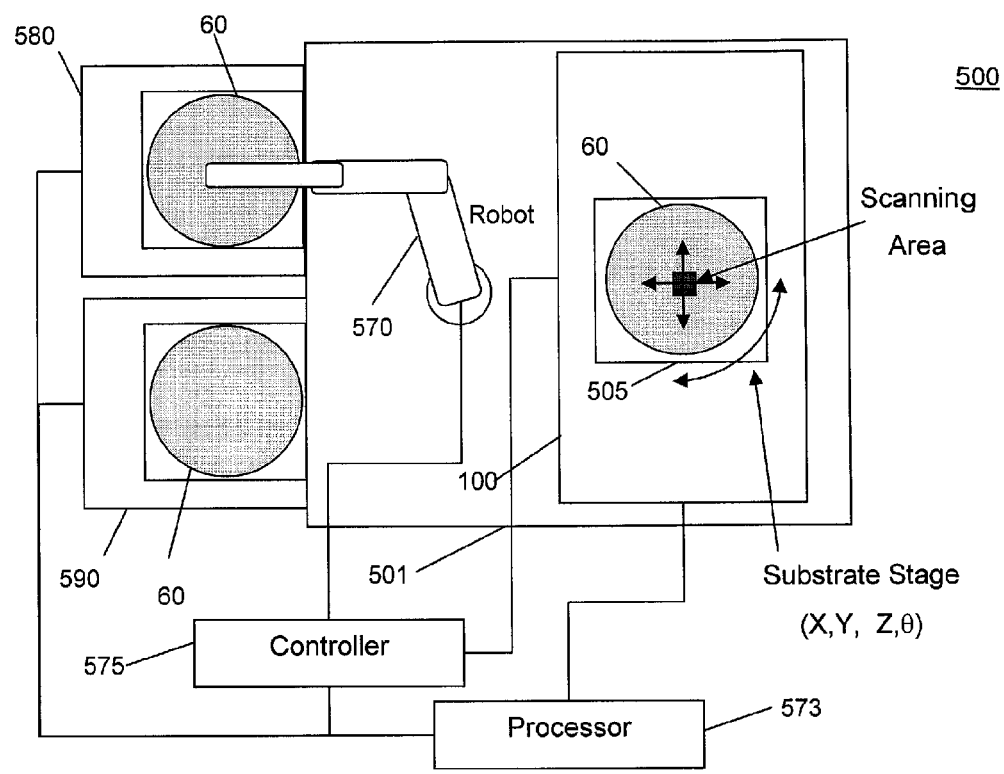
FIG. 5 is an illustration of a substrate processing station in accordance with an embodiment of the disclosure.

FIG. 5 is an illustration of an exemplary substrate processing station 500 in accordance with an embodiment of the disclosure. Substrate processing station 500 includes substrate scanning system 100 and a sample handling system 501. Substrate processing station 500 further includes a sample handler 570, such as a robot arm, for example, a sample delivery cassette system 580, and a sample retrieval cassette system 590. Sample handler 570 acquires substrate 60 from delivery cassette system 580 and places substrate 60 on a substrate stage 505. Substrate stage 505 may be enabled to align substrate 60, or alternatively, an additional substrate alignment/orientation stage (not shown) may be provided separately in sample handling system 501. Alignment/orientation comprises X and Y translation in the plane of substrate stage 505, Z translation normal to the plane of stage 505, and rotation θ about the axis perpendicular to the X-Y plane. Z translation provides motion to enable change of position of substrate 60 relative to lens 40, such as for positioning focus spot 50 above, at or below the surface of substrate 60. Alternatively, lens 40 may be translatable in the Z direction, by means of piezo-motor or other well known mechanical translation stages. Sample handler 570 may also provide for transferring substrate 60 from the alignment stage to substrate stage 505. After substrate processing, substrate 60 is transferred by sample handler 570 from stage 505 to retrieval cassette system 590. Sample handling system 501 components including sample handler 570, delivery cassette system 580, and retrieval cassette system 590, may further be coupled to, and supervised by, a processor 573 and a controller 575. Alignment of substrate 60 may be performed on stage 505, or, alternatively, on a separate sample aligner (not shown) included in sample handling system 501. Sample handler 570 performs sample transport operations, including moving substrate 60 from delivery cassette system 580 to substrate scanning system 100, and then to retrieval cassette system 590. Details of a related sample handling system may be found in commonly-owned U.S. Pat. No. 6,568,899, entitled "Wafer Processing System Including a Robot", which is incorporated by reference in its entirety.

Figure 6:
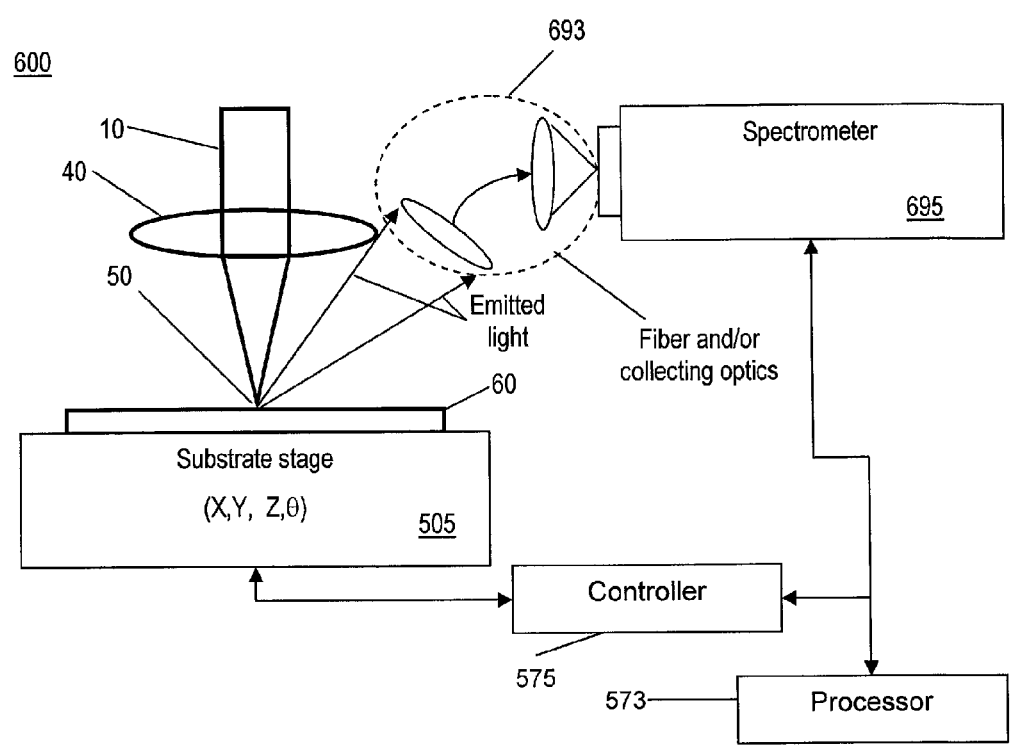
FIG. 6 is an illustration of a laser optical spectroscopy system in accordance with an embodiment of the disclosure.

FIG. 6 is an illustration of a laser optical spectroscopy system 600 in accordance with an embodiment of the disclosure. System 600 includes laser beam 10 directed to substrate 60 via flat field lens 40 or similar objective focusing optics to provide focused spot 50. Substrate 60 is disposed on a substrate stage 505, which is adapted to provide X, and Y movement in the plane of stage 505, Z translation normal to stage 505, and angular rotation θ of substrate 60 about the axis normal to the substrate. Alternatively, lens 40 (FIG. 1) may be translated by means of a piezo-motor or other well know types of mechanical translation stages to provide the same effective Z relative translation between substrate 60 and focus spot 50. In addition, goniometric orientation capability (not shown), may be provided to permit orientation of substrate 60 to be either normal or non-normal to laser beam 10.

Z translation enables positioning of substrate 60 relative to focus spot 50 above, at or below the surface of substrate 60. For example, if beam 10 is of sufficient energy, and focused to spot 50 at a depth beneath the surface of substrate 60 that gradually increases, material from substrate 60 may be ablated as a function of depth. A portion of light emission from focused spot 50 on substrate 60 resulting from illumination from laser beam 10 is directed by collecting optics 693 to the input of a spectrometer 695 for spectral analysis of the emitted light components. If, for example, the collected light results from optical emission as focused spot 50 from light beam 10 ablates material at increasing depth beneath the surface of substrate, optical emission spectra may be obtained as a function of depth, which provides subsurface material characterization information.

Collecting optics 693 may include a combination of lenses and mirrors (not shown) and may further include filters and other standard optical components to provide the collected light emission to the spectrometer. Collecting optics 693 may further include optical fiber (not shown) and associated optical components to perform the same or equivalent functions. System 600 may further include interfaces between controller 575, processor 573, and spectrometer 695.

Figure 7:
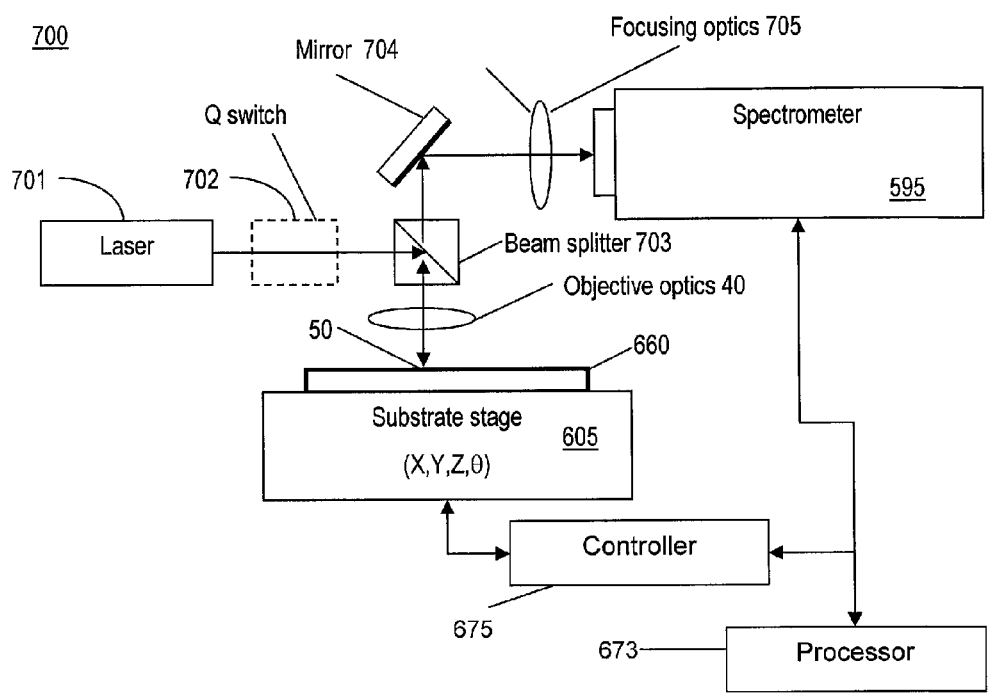
FIG. 7 is an illustration of a laser optical spectroscopy system in accordance with an embodiment of the disclosure.

FIG. 7 is an illustration of another laser optical spectroscopy system in accordance with an embodiment of the disclosure. System 700 is generally similar to system 600 with the following exceptions. A laser 701, which may be single wavelength or multi-wavelength, may be CW. Alternatively, laser 701 may be pulsed, with a specific pulse width and duty cycle. Pulse formation may be achieved using a Q switch 702 configured with laser 701. System 700 further differs from system 600 in at least that laser beam 10 is provided to substrate 60 by means of a beam splitter/combiner 703, such as a cube prism or a partially reflecting mirror, to direct beam 10 through objective (or flat field) lens optics 40 (which may be equipped with Z translation, as described above) to focused spot 50 at or relative to the surface of substrate 60. In system 700, in contrast to system 600, light emitted from substrate 60 is collected through the same optics 40, is at least partially transmitted through beam splitter/combiner 703, and is directed to spectrometer 595 by means of at least one mirror 704 and focusing optics 705. This arrangement may be beneficial as a more compact arrangement of optical components. Note that substrate 60 can be or comprise a semiconductor material, a conductor, or an insulator.

Figure 8:
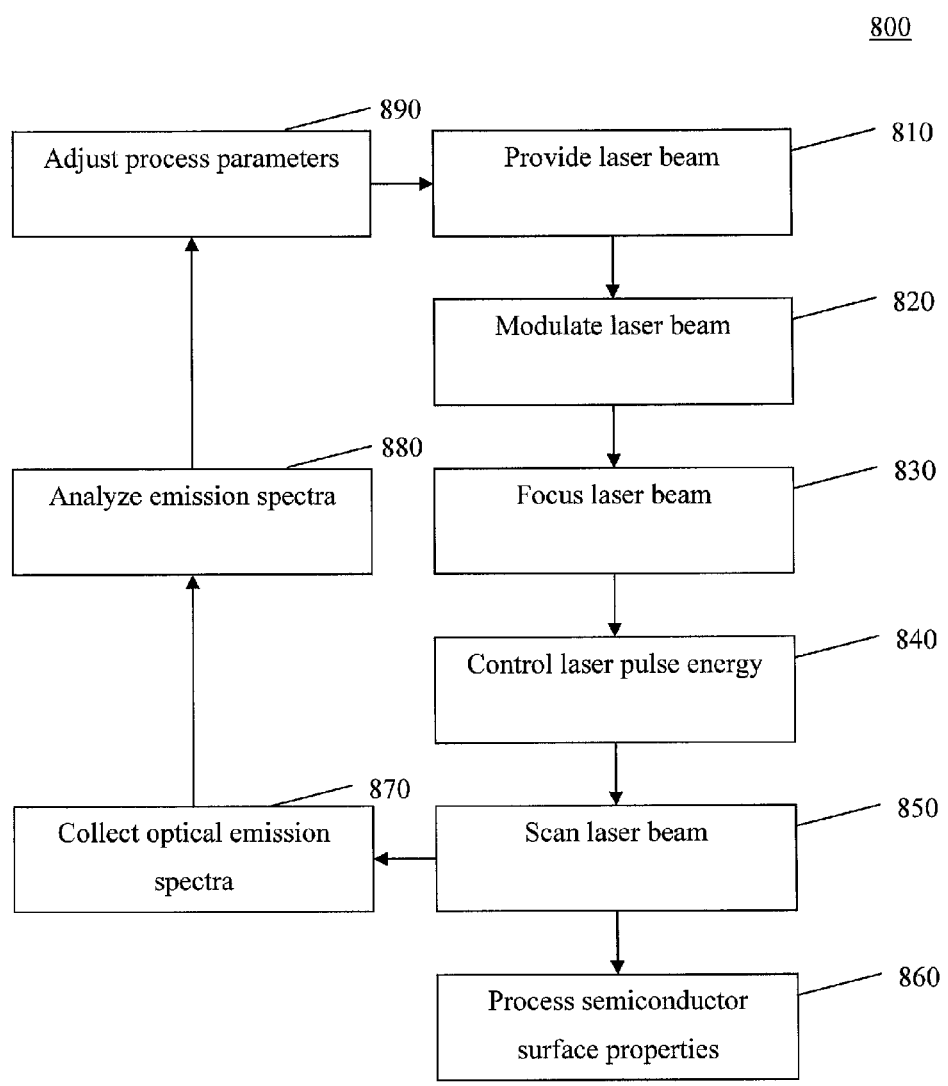
FIG. 8 is a diagram of the method of controlling the processing of semiconductor materials and devices on the basis of optical emission spectroscopy in accordance with an embodiment of the disclosure.

FIG. 8 is a diagram of the method of controlling the processing of semiconductor materials and devices on the basis of optical emission spectroscopy in accordance with an embodiment of the disclosure. Method 800 is generally similar to method 200 with the following exceptions. Light spectra emitted during a beam scanning 850 are collected 870 and analyzed 880 in spectrometer 595. Based on the analysis obtained, processor 573 and controller 575 may adjust process parameters 890 accordingly to optimize the desired results. This process can be iterative or continuous to continually adjust parameters or monitor and maintain desired settings. The laser can be adjusted such that spectra from a desired depth of the substrate or device is analyzed. As a result, properties at specific locations and depths of the substrate can be analyzed and process parameters adjusted if needed. Note that in the embodiments of FIGS. 6-8, the laser beam does not need to be scanned in a pattern or otherwise. A simple spot illumination can be used to obtain emission spectra from a single spot on the substrate.

Figure 9:
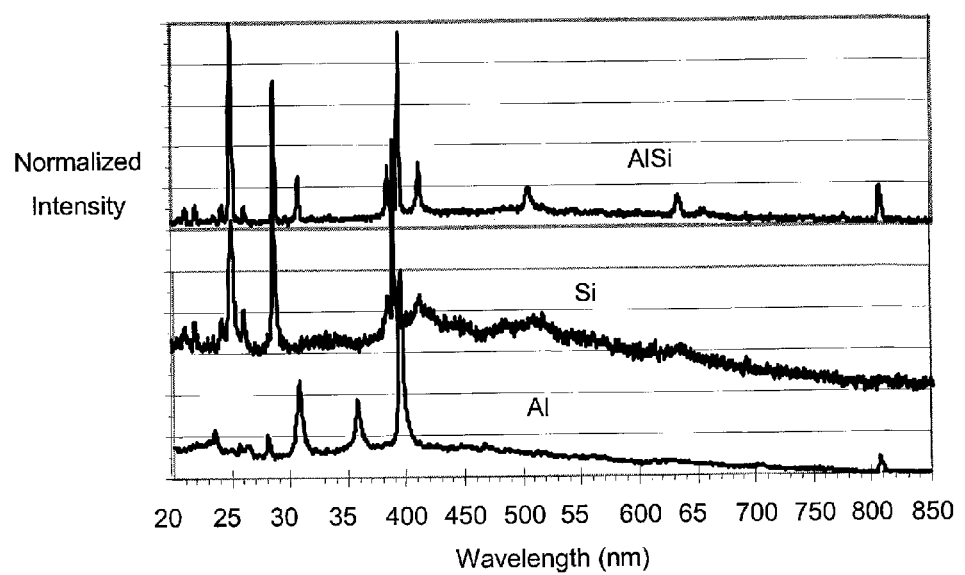
FIG. 9 is an example of optical emission spectra obtained in accordance with an embodiment of the disclosure.

An example of optical emission spectroscopy is shown in FIG. 9. Optical spectra of samples of Al, Si, and AlSi are superimposed in the same graph of normalized intensity (where each trace is offset for viewing convenience. Measurements were made under ambient atmospheric conditions. Laser beam 10 was initially CW, but an optical modulator provided a delivered beam of 1064 nm wavelength light with pulse widths approximately from 2 to 50 nanoseconds, at a duty cycle approximately between 5% and 50%. Laser pulse power was between 50 and 100 kW. The spot size may vary from approximately 1 to 40 micrometers. Since the measurement was for the purpose of depth profiling, there was no scanning of the substrate area, and the spot location was stationary. The focal length varied from 100 mm to 400 mm, with a shorter focal length producing a smaller spot size and shorter depth of field focus. Signal-to-noise in the spectral emission signal is improved by integrating the signal over time, particularly with modulation spectroscopy, which is the case here. Typical integration times may be from approximately 1 ms to 100 ms.

Referring to FIG. 9, as material is removed from the surface, the spectral emission will change as the atomic or molecular species that emit radiation changes. For example, the lower trace of FIG. 9 provides the spectrum of Al, which may be the result of an ablative removal of aluminum from a portion of a substrate. When the ablative removal of Al on a Si substrate is complete, the spectrum obtained will look like the middle trace, i.e., a Si spectrum. Detection of the interface between the two materials is evident in the upper trace, where the spectrum descriptive of AlSi show features of both atomic species, as well as possible additional, more complex structure.

In implementations, the above described techniques and their variations may be implemented at least partially as computer software instructions operational in processor 573 and controller 575. Such instructions may be stored on one or more machine-readable storage media or devices and are executed by, e.g., one or more computer processors, or cause the machine, to perform the described functions and operations. Processor 573 may generate scripts to control all components of exemplary substrate processing station 500, optical emission system 600 or 700. For example, the script may generate a set of scanning path 420 commands within segment 410, and an X-Y translation and/or θ rotation commands to substrate stage 505, typically via controller 575. Furthermore, focused laser beam processing may be accomplished by a simultaneous combination of operations of substrate scanning system 100 and substrate stage 505 under direction from processor 573. Additional control processes may be contemplated within the scope of the disclosure. The laser beam can be from a conventional laser scriber or any suitable laser system.

Also, only those claims which use the word "means" are intended to be interpreted under 35 USC 112, sixth paragraph. Moreover, no limitations from the specification are intended to be read into any claims, unless those limitations are expressly included in the claims. Accordingly, other embodiments are within the scope of the following claims. For example, the above describes certain methods for laser scanning; however, any suitable laser beam scanning mechanism may be used including vibrating mirrors, rotating mirrors, galvo mirror systems, and/or piezo micro position control systems.

What is claimed is:

1. A method of material processing comprising:
providing a laser beam of a selected wavelength and a selected peak power;
focusing the laser beam to a desired depth of a material;
controlling to a selected value the total energy in the laser;
scanning the laser beam in a programmed pattern over a surface of the material; and
collecting optical emission spectra from the material to determine material characteristics at the desired depth.

2. The method of claim 1, wherein the selected wavelength is approximately between 140 nanometers and 3 microns.

3. The method of claim 1, wherein the laser beam is a continuous beam.

4. The method of claim 1, wherein the laser beam is modulated to provide a discrete pulse width approximately between 10 femtoseconds and 100 milliseconds.

5. The method of claim 4, wherein the modulating comprises selecting a pulse repetition rate to provide a selected average power delivered in the laser beam to the surface of the material.

6. The method of claim 5, wherein the selecting the pulse repetition rate comprises selecting a duty cycle that is a percentage corresponding to a fraction of the discrete pulse width divided by a period corresponding to the pulse repetition rate wherein the period is an inverse of the pulse repetition rate.

7. The method of claim 1, wherein the focusing comprises forming an effective beam diameter approximately between 0.1 micrometer and 1 millimeter.

8. The method of claim 4, wherein the total energy per pulse selected is between 1 micro-Joule and 1 Joule.

9. The method of claim 1, wherein the scanning comprises:
providing a first scanning area of the surface of the material;
directing the focused laser beam along a first programmed path within the first scanning area;
blocking the focused laser beam upon completion of scanning the first scanning area;
providing a second scanning area of the surface of the material; and
directing the focused laser beam along a second programmed path within the second scanning area.

10. The method of claim 9, wherein the area of the first and second scanning areas is between 7840 nanometer$^2$ and 400 cm$^2$.

11. The method of claim 1, wherein the collecting comprises directing light emitted from the material to a spectrometer.

12. The method of claim 1, further comprising controlling a material process on the basis of the collected optical emission spectra.

13. The method of claim 12, wherein the controlling comprises adjusting at least one process parameter of the process.

14. The method of claim 9, wherein the first and second programmed paths are the same.

15. The method of claim 14, wherein the programmed pattern comprises the first and second programmed paths and a path for scanning a plurality of scanning areas on the surface of the material.

16. The method of claim 15, wherein the plurality of scanning areas comprises the entire surface of the material.

17. The method of claim 1, wherein the material comprises a semiconductor, an insulator, or a conductor.

18. The method of claim 1, wherein the processing is in-situ.

19. The method of claim 1, wherein the material characteristics are used for chemical composition analysis, depth profiling, spatial homogeneity characterization, purity, or reactivity.

20. The method of claim 1, wherein the focusing ablates the material at the desired depth.

21. The method of claim 1, wherein a scanned area of the surface of the material ranges between 7840 nanometer$^2$ and 400 cm$^2$.

22. A sample process monitoring and control system, comprising:
a laser system;
a sample scanning system adapted to direct a focused beam from the laser to a desired depth of a sample;
an optical spectrometer adapted to characterize the processing of the sample based on optical emission spectra;
optical elements adapted to couple the optical emission spectra obtained from the sample to the optical spectrometer;
a controller adapted to control operations of the sample scanning system and the optical spectrometer; and
a processor adapted to interface with the controller, the sample scanning system, and the optical spectrometer, wherein the processor provides instructions to the controller and generates a processing script for operations of a processing system based at least on the obtained optical emission spectra.

23. The system of claim 22, wherein the laser beam has a wavelength between 140 nanometers and 3 micrometers.

24. The system of claim 22, wherein a scanned area of the sample ranges between 7840 nanometer$^2$ and 400 cm$^2$.

25. The system of claim 22, wherein the laser beam is provided continuously.

26. The system of claim 22, wherein the laser beam is modulated to provide a pulse width between 10 femtoseconds and 100 milliseconds at a pulse repetition rate duty cycle that is a percentage corresponding to a fraction of the pulse width divided by a period corresponding to a pulse repetition rate wherein the period is an inverse of the pulse repetition rate.

27. The system of claim 26, wherein the laser beam has a selected total energy per pulse between 1 micro-Joule and 1 Joule.

28. The system of claim 22, wherein the sample scanning system comprises a sample holding stage adapted to translate the sample in X and Y directions in the plane of the sample holding stage, translate the sample in the Z direction normal to the plane of the sample holding stage, and angularly rotate the sample about the Z direction.

29. The system of claim 28, wherein the sample holding stage is adapted to permit orientation of the sample to be either normal or non-normal to the focused laser beam.

30. The system of claim 22, wherein the focused laser beam ablates material from the sample at the desired depth.

31. The system of claim 22, further comprising a lens adapted to move linearly relative to the sample to focus the laser beam to a desired depth.

32. The system of claim 31, wherein the laser beam ablates material from the sample at the desired depth.

* * * * *